United States Patent [19]
Graumann

[11] Patent Number: 6,139,183
[45] Date of Patent: Oct. 31, 2000

[54] X-RAY EXPOSURE SYSTEM FOR 3D IMAGING

[75] Inventor: Rainer Graumann, Hoechstadt, Germany

[73] Assignee: Siemens Aktiengesellschaft, Munich, Germany

[21] Appl. No.: 09/174,159

[22] Filed: Oct. 16, 1998

[30] Foreign Application Priority Data

Oct. 17, 1997 [DE] Germany .............. 197 46 092

[51] Int. Cl.[7] .............. H05G 1/02
[52] U.S. Cl. .............. 378/206; 378/198
[58] Field of Search .............. 378/205, 206, 378/198

[56] References Cited

U.S. PATENT DOCUMENTS

| | | | |
|---|---|---|---|
| 5,014,293 | 5/1991 | Boyd et al. | 378/198 |
| 5,109,397 | 4/1992 | Gordon et al. | |
| 5,706,324 | 1/1998 | Wiesent et al. | |
| 5,772,594 | 6/1998 | Barrick | 378/205 |
| 6,007,243 | 12/1999 | Ergun et al. | 378/198 |

FOREIGN PATENT DOCUMENTS

| | | |
|---|---|---|
| OS 360 4955 | 8/1987 | Germany . |
| OS 195 35 583 | 3/1997 | Germany . |

Primary Examiner—Craig E. Church
Attorney, Agent, or Firm—Hill & Simpson

[57] ABSTRACT

An X-ray exposure system has a mobile X-ray apparatus with an X-ray source and an X-ray receiver that are adjustable relative to a subject for registering successive 2D projections of the subject from different projection directions, an arrangement disposed outside the beam path of the X-ray beam emanating from the X-ray source for directly determining the projection geometries of the X-ray source and of the X-ray receiver at the points in time of the individual 2D projections, and a computer supplied with signals from the arrangement for the direct determination of the projection geometries, which reconstructs 3D images of the subject from the 2D projections.

5 Claims, 1 Drawing Sheet

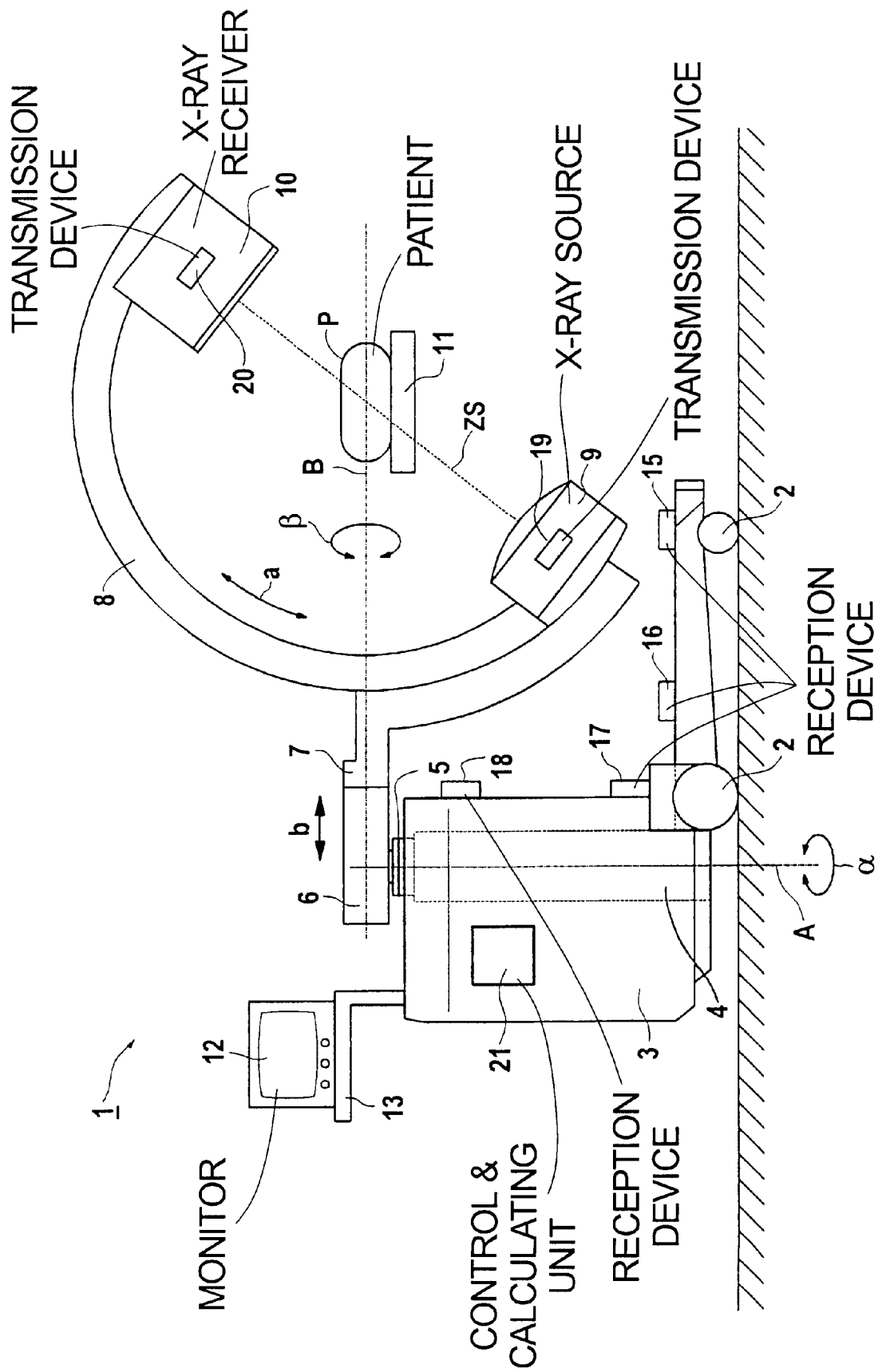

X-RAY EXPOSURE SYSTEM FOR 3D IMAGING

BACKGROUND OF THE INVENTION

1. Field of the Invention

The present invention is directed to an X-ray exposure system of the type having an X-ray apparatus with an X-ray source and an X-ray receiver that are adjustable relative to the subject for registering successive 2D projections of a subject from different projection directions, and means for reconstructing 3D images of the subject from the 2D projections.

2. Description of the Prior Art

X-ray exposure systems of this type usually have an X-ray apparatus with a C-arm for carrying the X-ray source and the X-ray receiver, this C-arm being seated in a holder at the X-ray apparatus so as to be motor-adjustable in a specific angular range along its circumference (orbital motion). For acquiring 2D projections from different projection angles for 3D image reconstruction of, for example, a body region of a subject with the C-arm X-ray apparatus, the C-arm, after appropriate placement relative to the subject to be examined, is adjusted along its circumference during the registration of 2D projections of the body region of the subject. 3D images of the body region of the subject are subsequently reconstructed from the 2D projections registered with the X-ray apparatus during the adjustment motion of the C-arm. The reconstruction of 3D images, however, assumes exact knowledge of the projection geometry, i.e. the exact knowledge of the position of the X-ray source and the X-ray receiver and of the projection angle during each of the individual 2D projections.

Known C-arm X-ray apparatuses exhibit mechanical instabilities particularly relating to the adjustment of the C-arm along its circumference, as a result of which deviations of the real adjustment motion of the C-arm from the ideal adjustment motion occur. The determination of the projection geometries is thereby often affected by errors, the quality of the 3D images reconstructed from the 2D projections suffering therefrom.

German OS 195 12 819, for example, discloses an X-ray computed tomography apparatus for 3D imaging that has an X-ray source that emits a conical X-ray beam penetrating a measurement field. A subject to be examined that is arranged in the measurement field is penetrated by the X-ray beam, which strikes a planar detector whose output signals are supplied to a computer for the reconstruction of 3D images of the subject. For determining the projection geometries of the X-ray source and of the detector at the point in time of the individual 2D projections, two rings provided with metal structures are provided, these being arranged above and below the region of the subject to be examined. The metal structures of the rings are visible in the 2D projections of the body region to be examined, so that the respective projection geometries of the 2D projections can be calculated from their position.

This method for determining the projection geometries, however, has the disadvantage that the rings have a relatively large diameter, so that the spacing between the X-ray source and the rings is very small (a few centimeters). The metal structures therefore appear greatly enlarged in the 2D projections, so that large parts of the 2D projections are overlaid by the metal structures. Further, only a small region of the metal structures of the rings is imaged in the 2D projections, so that the determination of the projection geometries is difficult on the basis of the slight number of imaged metal structures.

U.S. Pat. No. 5,109,397 discloses a mobile computed tomography apparatus having an X-ray arrangement rotating around a rotation center and comprising an X-ray source and an X-ray receiver. Sensors are allocated to this X-ray arrangement, these sensors moving along with the X-ray arrangement and interacting with a stationary ring allocated to the rotation center for detecting lateral movements of the X-ray arrangement during a scan. The sensors thereby generate signals whose evaluation allows the spacings between their defined point of attachment and the ring to be determined. The acquired data are subsequently utilized in the reconstruction of tomograms. The ring is thereby arranged in the propagation path of an X-ray beam emanating from the X-ray source. In another embodiment of this computed tomography apparatus, the ring can be provided with X-ray-positive marks that are imaged in the 2D projections, whereby their interpretation enables the determination of the projection geometries.

German OS 36 04 955 discloses an X-ray diagnostic apparatus having an image generating system with an X-ray radiator and radiation receiver as well as a patient table. Position sensors in the form of potentiometers that acquire the position of adjustable components of the image generating system are connected to these components. The potentiometers, however, are not suited for the exact determination of the projection geometries.

German OS 195 35 583 also discloses an X-ray diagnostic apparatus with a positioning aid. A light transmitter for emitting a light beam is provided at an X-ray image intensifier so that this light beam is focused onto a X-ray radiator lying opposite the X-ray image intensifier. In this way, a positioning of the X-ray radiator and the X-ray image intensifier can ensue with reference to an examination subject without emitting X-rays.

SUMMARY OF THE INVENTION

An object of the present invention is to provide an X-ray exposure system of the type initially described which can be flexibly employed for 3D imaging and wherein the radiation dose for the patient is reduced.

This object is inventively achieved by an X-ray exposure system having a mobile X-ray apparatus with an X-ray source and an X-ray receiver that are adjustable relative to a subject for registering successive 2D projections of the subject from different projection directions, having a projection geometry acquisition arrangement disposed outside the beam path of the X-ray beam emanating from the X-ray source for directly acquiring the projection geometries of the X-ray source and of the X-ray receiver at the points in time of the individual 2D projections, and means collaborating with the arrangement for the direct acquisition of the projection geometries for reconstructing 3D images of the subject from the 2D projections. The use of the X-ray exposure system with a mobile X-ray apparatus for the registration of successive 2D projections with an X-ray arrangement that is adjustable relative to a subject, and which carries an X-ray source and an X-ray receiver, enables a flexible and location-independent utilization of the X-ray exposure system for 3D imaging. The arrangement for the direct acquisition of the projection geometries, which are required due to mechanical instabilities of mobile X-ray apparatus occurring in the adjustment of the X-ray arrangement, are arranged outside the beam path of the X-ray beam. Since the arrangement for the acquisition of the projections geometries thus need not be imaged in X-ray images, an enlargement of the aperture angle—as in the known X-ray computer tomography systems—is also not necessary, allowing the radiation dose for the subject to be reduced. As used herein, direct acquisition of the projection geometries means acquisition using components which are attached at the X-ray apparatus itself, for example avoiding the use of position sensors at the X-ray apparatus. Due to the aforementioned instabilities in the adjustment of the X-ray source and of the X-ray receiver, conventional acquisition components would not be able to exactly determine the positions of the X-ray source and of the X-ray receiver.

Inventively, the direct acquisition of the positions of the X-ray source and of the X-ray receiver are, for example, is accomplished by transmission and reception devices according to one version of the invention. The reception devices are preferably arranged at stationary parts of the X-ray apparatus and the transmission devices can be arranged in the region of the X-ray source and of the X-ray receiver, or at these components themselves, so that they can be co-moved with the X-ray source and the X-ray receiver during the course of an adjustment motion of these components. During the adjustment motion with simultaneous registration of 2D projections from different projection directions, the transmission devices emit output signals per registration of a 2D projection that are received by the reception devices. The interpretation of the received signals subsequently enables the determination of the exact positions of the X-ray source, of the X-ray receiver and of the projection angle for every registration of a 2D projection.

In another version of the invention, the means for the reconstruction of 3D images include a control and calculating unit collaborating with the arrangement for the direct acquisition of the positions of the X-ray source and of the X-ray receiver. The control and calculating unit preferably determines the positions of the X-ray source and of the X-ray receiver for each of the 2D projections and subsequently employs the identified positions for the reconstruction of 3D images from the 2D projections.

In a further version of the invention the X-ray apparatus of the X-ray exposure system includes an arm which carries the X-ray source and the X-ray receiver and a holder for the arm, with the arm being seated at the holder so as to be displaceable along its circumference. The X-ray apparatus of the X-ray exposure system can thus be a known C-arm X-ray apparatus that is provided with appropriate means for the reconstruction of 3D images and an arrangement for the direct acquisition of the positions of the X-ray source and of the X-ray receiver at the points in time of the individual 2D projections. The use to a known X-ray apparatus for the X-ray exposure system improved according tot he invention enables the overall costs for such an X-ray exposure system to be kept low.

DESCRIPTION OF THE DRAWING

The single FIGURE is a schematic illustration of an embodiment of an x-ray exposure system for 3D imaging constructed and operating in according with the principles of the present invention, having a mobile C-arm X-ray apparatus.

DESCRIPTION OF THE PREFERRED EMBODIMENTS

The C-arm X-ray apparatus 1 shown in the FIGURE has an apparatus cart 3 movable on wheels 2 and having a lifting mechanism 4, that is only schematically indicated in the FIGURE. The lifting mechanism 4 is provided with a column 5 having a longitudinal axis A around which the column 5 can be turned in the direction of the double arrow α. A holding part 6 is arranged at the column 5, a holder 7 for supporting a C-arm 8 being in turn arranged at this holding part 6. The C-arm 8 carries an X-ray source 9 and an X-ray receiver 10 opposite one another at its two ends, that are arranged relative to one another so that a central ray ZS of an X-ray beam emanating from the X-ray source 9 strikes the X-ray receiver 10 approximately centrally. In a known way, the C-arm 8 is seated at the holder 7 so as to be adjustable manually or motor-driven in the direction of the double arrow a along its circumference in a way not shown in greater detail (orbital motion). In a known way, the holder 7 is rotatable around a common axis B of the holding part 6 so as to be and of the holder 7 (see the double arrow β, angulation motion) and is seated at the holding part 6 displaceable in the direction of the axis B (see double arrow b). With the assistance of the lifting device 4, the C-arm 8, which is connected to the column 5 of the lifting device 4 via the holder 7 and the holding part 6, is vertically adjustable relative to the apparatus cart 3.

In the present exemplary embodiment, the C-arm X-ray apparatus 1 is provided for producing 3D images of a body region of a patient P (only schematically shown in the FIGURE) lying on a patient bed 11. The 3D images are reconstructed from 2D projections of the body region from different projection directions that are acquired with the assistance of the X-ray source 9 and the X-ray receiver 10, and can be displayed with a monitor 12 that is arranged on a holder 13 of the C-arm X-ray apparatus 1.

For registering 2D projections from different projection angles, the C-arm 8 is motor-adjusted along its circumference in the direction of the double arrow a in an angular range of approximately 200° around the body region of the patient P to be examined and visually displayed, with approximately 50 through 100 2D projections of the body region of the patient P being registered from different projection directions.

Since, as already mentioned, C-arm X-ray apparatuses exhibit mechanical instabilities, such as during adjustment of the C-arm along its circumference, the system shown in the FIGURE includes an arrangement for directly acquiring the projection geometries of the X-ray source 9 and of the X-ray receiver 10 at the points in time of the individual 2D projections. This arrangement is disposed outside the beam path of an X-ray beam emanating from the X-ray source 9 and allows the exact determination of the different projection geometries of the 2D projections. In the present exemplary embodiment, the arrangement for directly acquiring the projection geometries includes transmission and reception devices that are arranged at components of the C-arm X-ray apparatus 1. The C-arm X-ray apparatus 1 has a number of reception devices arranged at the apparatus cart 3 that is stationary relative to the C-arm 8. In the present exemplary embodiment, the X-ray source 9 as well as the X-ray receiver 10 are respectively provided with a transmission devices 19, 20 that are co-moved with the X-ray source 9 and the X-ray receiver 10 given adjustment of the C-arm 8 along its circumference.

A control and calculating unit 21 of C-arm X-ray apparatus 1, which both controls the motor-adjustment of C-arm 8 and triggers the registration of 2D projections, also controls the triggering of signals of the transmission devices 19, 20 simultaneously with the triggering of a 2D projection.

On the basis of the signals received with the reception devices 15 through 18 that are respectively emitted by the transmission devices 19, 20 at the point in time of the triggering of a 2D projection, the projection geometries of the X-ray source 9 and of the X-ray receiver 10 can be determined with the control and calculating unit 21 for each 2D projection. The signals received by the reception devices 15 through 18 are directly supplied to the control and calculating unit 21 for determining the projection geometries of the X-ray source 9 and of the X-ray receiver 10. The projection geometries determined in this way are subsequently utilized for the reconstruction of 3D images of body regions of the patient P that, as already mentioned, can be visually displayed on the monitor 12 of C-arm X-ray apparatus 1.

The signal lines of the control and calculating unit 21 for the transmission of the control signals for the motor-adjustment of C-arm 8, for triggering 2D projections, for triggering signals by the transmission devices 19, 20 as well as for the transfer of the signals received by the reception devices 15 through 18, are not shown in the FIGURE.

The number of transmission and reception devices provided for the positional determination of the X-ray source 9 and of the X-ray receiver 10 can deviate from the number employed in the present exemplary embodiment.

Further, the attachment of the transmission and reception devices to C-arm X-ray apparatus 1 is to be understood as merely exemplary and can also be differently implemented. In particular, the reception devices can alternatively be arranged at the X-ray source 9 and the X-ray receiver 10 and the transmission devices can be arranged at the apparatus cart 3. For example, transmitters and receivers that operate on the basis of acoustic waves, for example ultrasound, or electromagnetic waves, for example microwaves or light, can be provided as the transmission and reception devices.

An advantage of the inventive X-ray exposure system with the mobile C-bend X-ray apparatus 1, the transmission devices 19, 20 and the reception devices 15 through 18 is that the X-ray exposure system can be utilized for 3D imaging independently of location, for example in operating rooms as well, with tedious alignment procedures between C-arm X-ray apparatus and the arrangement for directly acquiring the projection geometries being avoided as a result of the inventive embodiment. Moreover, no imagings of X-ray-positive marks in the 2D projections are required for determining the projection geometries, so that the aperture angle of the X-ray beam need not be larger than absolutely required for imaging the relevant body region of the patient P, allowing the radiation dose for the patient P to be reduced.

The arrangement for directly acquiring the projections geometries, moreover, need not necessarily be formed by transmission and reception devices, but can instead employ other components arranged outside the beam path of the X-ray beam that enable the determination of the projection geometries.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray exposure system comprising:
    a mobile cart;
    an X-ray apparatus mounted on said mobile cart, said X-ray apparatus including an X-ray source and an X-ray receiver, said X-ray source emitting an X-ray beam which proceeds along a beam path and strikes said X-ray receiver, and support means on which said X-ray source and said X-ray receiver are mounted for moving said X-ray source and said X-ray receiver relative to an examination subject for obtaining a plurality of successive 2D projections of said examination subject respectively from a plurality of different projection directions, each of said 2D projections having a unique projection geometry of the X-ray source and the X-ray receiver at a point in time at which the respective 2D projections are obtained, said support means having a mechanical instability associated therewith which precludes accurate identification of the projection geometry via said support means;
    means disposed outside of said beam path for directly acquiring the respective projection geometries for said plurality of 2D projections; and
    computer means supplied with said plurality of projection geometries from said means for directly acquiring the respective projection geometries, for reconstructing a 3D image of said examination subject from said plurality of 2D projections.

2. An X-ray exposure system as claimed in claim 1 wherein said means for directly acquiring the respective projection geometries comprises at least one transmitter communicating with at least one receiver.

3. An X-ray exposure system as claimed in claim 2 wherein said at least one transmitter is attached to said means for moving said X-ray source and said X-ray receiver, and wherein said at least one receiver is mounted on said mobile cart.

4. An X-ray exposure system as claimed in claim 1 wherein said computer means comprises a control and calculating unit, disposed on said mobile cart, for reconstructing said 3D image.

5. An X-ray exposure system as claimed in claim 1 wherein said support means comprises a C-arm carrying said X-ray source and said X-ray receiver, and having a circumference, and a holder, mounted on said mobile cart, in which said C-arm is displaceable along said circumference.

* * * * *